(12) United States Patent
Roe et al.

(10) Patent No.: US 6,498,953 B2
(45) Date of Patent: Dec. 24, 2002

(54) BIOFEEDBACK DEVICE FOR AN INCONTINENT PERSON

(75) Inventors: Donald C. Roe, West Chester, OH (US); Peter Coles, Francavilla al Mare (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/866,438

(22) Filed: May 29, 2001

(65) Prior Publication Data

US 2001/0025147 A1 Sep. 27, 2001

Related U.S. Application Data

(62) Division of application No. 09/342,289, filed on Jun. 29, 1999, now Pat. No. 6,266,557.

(51) Int. Cl.[7] .................................................. A61N 1/36
(52) U.S. Cl. ........................... 607/41; 607/62; 128/905; 128/886
(58) Field of Search ............................. 600/29, 30, 587, 600/591, 593, 595, 546; 128/905, 885, 886; 607/1, 2, 39, 40, 41, 133, 138, 143, 62

(56) References Cited

U.S. PATENT DOCUMENTS 3,628,538 A * 12/1971 Vincent et al. ............. 600/546
4,063,548 A * 12/1977 Klatt et al. .................. 600/546

* cited by examiner

Primary Examiner—George R. Evanisko
(74) Attorney, Agent, or Firm—Michael P. Hayden; David M. Weirich; Ken K. Patel

(57) ABSTRACT

A biofeedback device for predicting an impending elimination of bodily waste in an incontinent person includes a sensing element in contact with an area of a user so as to detect electrical activity of a sphincter muscle associated therewith and a signaling element operatively connected to the sensing element that provides a signal upon an occurrence of a predetermined electrical activity for the sphincter muscle. The biofeedback device is able to predict an impending elimination of bodily waste for an incontinent person, as well as assist the incontinent person in achieving a contraction of his/her sphincter muscle.

28 Claims, 3 Drawing Sheets

BIOFEEDBACK DEVICE FOR AN INCONTINENT PERSON

This application is a division of application Ser. No. 09/342,289, filed Jun. 29, 1999, which matured into U.S. Pat. No. 6,266,557 issued on Jul. 24, 2001.

FIELD OF THE INVENTION

The present invention relates to devices utilized to monitor functions of the human anatomy and, more particularly, to a biofeedback device for an incontinent person which predicts an impending elimination of bodily waste and assists the incontinent person in achieving a contraction of his/her sphincter muscle.

BACKGROUND OF THE INVENTION

There are many products available to assist incontinent persons from the discomfort and distress associated with such condition, including disposable articles which are used to contain, isolate and dispose of bodily wastes. It will also be noted that some disposable articles even provide a signal after a defecation, urination or discharge event has occurred so that it can be changed promptly. These articles, while satisfactory for their intended purpose, are helpful only after the event has already occurred.

Accordingly, it has become recognized that an ability to predict when such an event is about to occur, in order that the incontinent person or a caregiver thereof can be prepared and take the necessary action before the event has taken place, would be advantageous over the prior products. One such attempt in this regard is disclosed in U.S. Pat. No. 5,416,469 to Colling, where a temperature sensor is imbedded in a diaper and connected to a sampling/recording meter. The meter measures and records the temperature of the sensor at specified time intervals over a predetermined period. In this way, the temperature and time data are able to be plotted on a graph and voiding events are identified. By applying this data over a sufficient time frame, the approximate time for future voiding events is then predicted. While the Colling method is an improvement in the art, it nevertheless still suffers from certain inherent inaccuracies. Not only does the method assume that an incontinent person will void within a calculated range of time, but it is also subject to other intervening actions (e.g., voluntary voiding, significant change in amount or time or intake of food, liquids, or drugs, or significant change in activity).

Therefore, a need exists for a device to more accurately predict and alert an incontinent person and/or their caregiver as to an impending elimination of bodily discharge. Moreover, such a device should optimally be utilized to assist an incontinent person in achieving an intentional, voluntary contraction of his/her sphincter muscle.

SUMMARY OF THE INVENTION

In accordance with a first embodiment of the present invention, a biofeedback device is disclosed as including a sensing element in contact with an area of a user so as to detect electrical activity of a sphincter muscle associated therewith and a signaling element operatively connected to the sensing element that provides a signal upon an occurrence of a predetermined electrical activity for the sphincter muscle.

In accordance with a second embodiment of the present invention, a method of predicting an impending elimination of bodily waste in an incontinent person is disclosed as including the following steps: identifying a specified electrical activity for a sphincter muscle of the incontinent person correlating to a contraction thereof, monitoring electrical activity of the sphincter muscle; and, determining whether the specified electrical activity occurs for the sphincter muscle. The method also preferably includes the step of providing a signal upon detection of the specified electrical activity.

In accordance with a third embodiment of the present invention, a method of assisting an incontinent person in achieving a contraction of his/her sphincter muscle is disclosed as including the following steps: identifying a specified electrical activity for the sphincter muscle correlating to an impending elimination of bodily waste; monitoring electrical activity of the sphincter muscle; determining whether the specified electrical activity for the sphincter muscle has occurred; and, providing a signal upon occurrence of the specified electrical activity.

A biofeedback device of the present invention may include any one or more of the above listed functions, and may also alternatively include other functions in addition to those examples given here.

Other features and advantages of the present invention are described with respect to the description of a preferred embodiment of the invention.

BRIEF DESCRIPTION OF THE DRAWINGS

While the specification concludes with claims particularly pointing out and distinctly claiming the subject matter that is regarded as the present invention, it is believed that the invention will be better understood from the following description, which is taken in conjunction with the accompanying drawings.

DETAILED DESCRIPTION OF THE INVENTION

The present invention relates to a biofeedback device utilized in predicting an impending elimination of bodily discharge and providing a signal in response thereto. In this way, the biofeedback device is able to alert an incontinent person and/or a caregiver so that appropriate action can be taken in response thereto, as well as assist an incontinent person in achieving and/or maintaining contraction of his/her sphincter muscle so as to provide at least temporary control of elimination. It will be understood for purposes of this invention that the term "incontinent person" includes children and babies, as well as adults, who have not yet mastered control of the sphincter muscle since the invention described herein may be utilized in conjunction with potty training.

As used herein, the term "biofeedback device" refers to devices which obtain data either directly or indirectly from a person's body and utilize such data to perform a desired function in response thereto. It will also be appreciated that the biofeedback device described herein, with the exception of the disposable electrodes, preferably be reusable. More specifically, the biofeedback device of the present invention preferably senses the electrical activity of a person's sphincter muscle and provides a signal upon the occurrence of a predetermined electrical activity correlating to an impending elimination of bodily waste.

Figure 1:
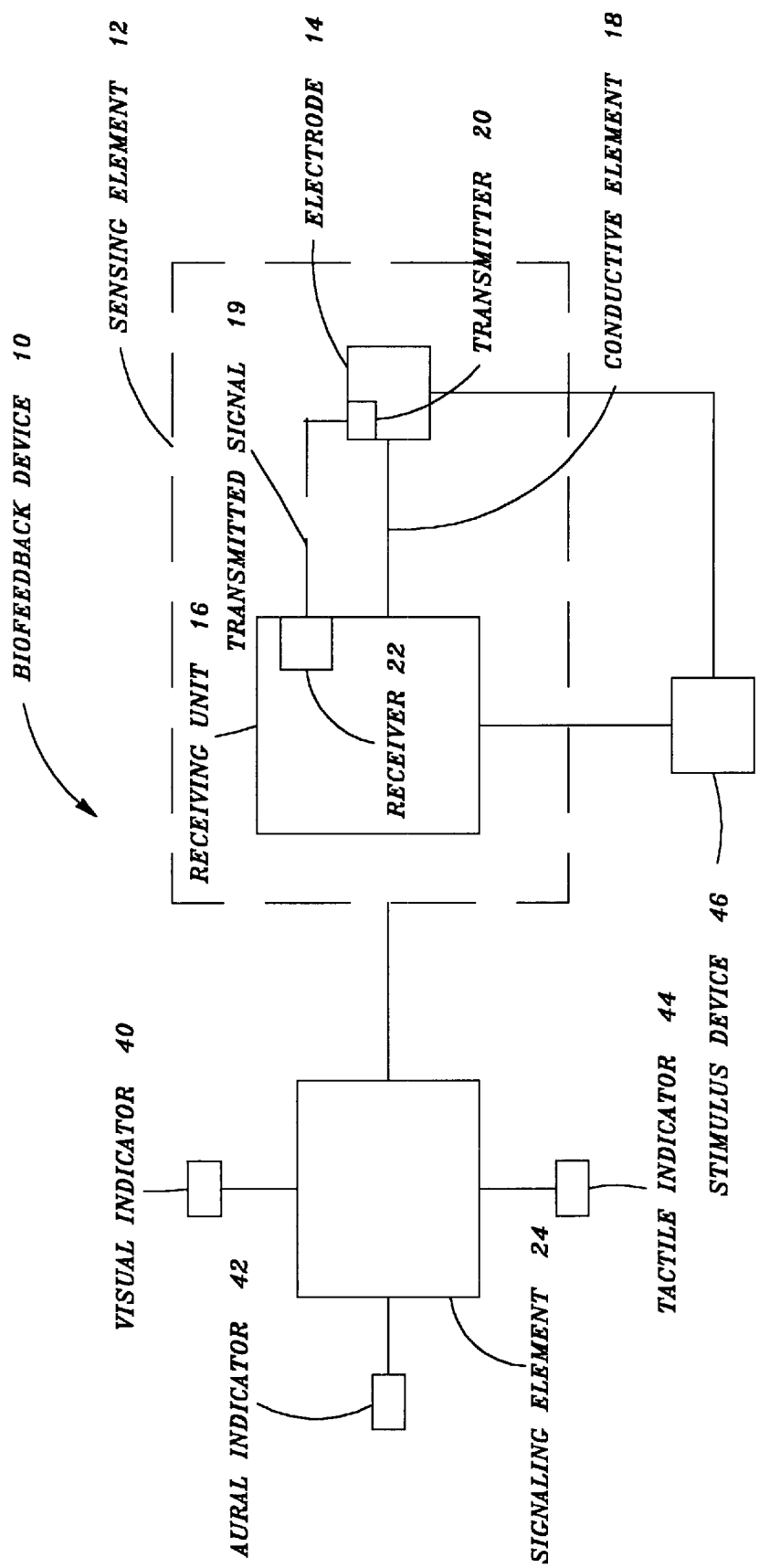
FIG. 1 is a block diagram of the biofeedback device of the present invention.

As seen in FIG. 1, biofeedback device 10 includes a sensing element, denoted generally by the reference numeral 12, which is in contact with an area of a person so as to detect electrical activity of a sphincter muscle associated therewith. It will be appreciated that such area may be the perianal area of the person to detect electrical activity of an external anal sphincter muscle or, alternatively, the perineal area of the person to detect electrical activity of an external urethral sphincter muscle. Although sensing element 12 may include any type of electrode 14 which is able to reliably provide the electrical activity of a sphincter muscle, such as needle electrodes, wire electrodes or an anal plug electrode, it is preferred that an adhesive surface electrode adhereable to the skin of the person be utilized to maintain uninterrupted contact with the wearer's skin. In this way, electrode 14 may be placed as close as possible to the intended area of the person (e.g., the anus) to detect electrical signals from the desired sphincter muscle (e.g., the external anal sphincter muscle, which is anatomically near the skin at the point of the anal orifice). It will be appreciated that one or more reference electrodes may be placed on the skin of the person near the above-mentioned regions or at remote sites, such as the thigh or abdomen.

An exemplary adhesive disposable surface electrode is manufactured by Dantec Medical A/S of Skovlunde, Denmark. Other suitable adhesive surface electrodes include electrodes available from Medicotest A/S of Olstykke, Denmark as M-00-S, N-00-S, M-00-A/F, Bs 3400, BS3500, BR, and BRS, as well as electrodes available from Multi Bio Sensor, Inc. of El Paso, Tex., as 3ST3, 3SG3-N, and 2DT2. Other suitable electrical sensors are disclosed in U.S. Pat. Nos. 5,785,040; 5,727,549; 5,337,748; 5,203,330; and 5,255,677, all of which are hereby incorporated by reference. If the sensor is not self-adhesive, an electroconductive, adhesive gel may be placed on electrode 14 of sensing element 12 before it is placed on the skin.

Sensing element 12 preferably includes a unit 16 operatively connected to electrode 14 for receiving and preferably displaying the electrical activity of the sphincter muscle adjacent thereto. One exemplary receiver unit is manufactured by Dantec Medical A/S and is known as Dantec EMG (Type 14 D11). It will be understood that sensing element 12, through electrode 14 and receiving unit 16, is preferably able to detect electrical activity of the sphincter muscle in a frequency range of approximately 5 Hertz to approximately 500 Hertz, and more preferably including a frequency range from about 10 Hertz to about 350 Hertz. Further, receiving unit 16 preferably is designed to permit user input and interaction so as to control the parameters of the predetermined electrical activity as discussed in greater detail herein.

In alternative embodiments, receiving unit 16 of the present invention may be any other commercially available EKG (electrocardiogram) or EMG (electromyogram) electrode and/or measuring system. For example, the MyoTrace 200, available from Noraxon U.S.A., Inc. of Scottsdale, Ariz., comprises a wideband electrode capable of sensing muscle electrical activity in the 16 Hertz to 500 Hertz range (this is appropriate for the slow-twitch muscles of the pelvic floor). Another commercially available EMG sensing system is the MyoSense system available from MIE Medical Research Ltd., of Leeds, U.K.

While sensing element 12 may optionally be integral with a disposable article, as disclosed in a pending application entitled "Disposable Article Having Proactive Sensors," Ser. No. 09/107,561, and an application filed concurrently herewith of the same title, each of which are owned by the assignee of the current invention and hereby incorporated by reference, it is intended in the present application that biofeedback device 10 be separate and reusable. Accordingly, electrode 14 may be directly connected to receiving unit 16 by means of a conductive element 18 or, as indicated by dashed line 19 in FIG. 1, receiving unit 16 may be located remotely from electrode 14 with communication therebetween provided via telemetry means (i.e., infrared, radio waves, or the like). Of course, this latter embodiment typically includes a transmitter 20 to be integrated with electrode 14 and a compatible receiver 22 located within receiving unit 16. The telemetry system may be any commercially available EMG or EKG telemetry system. One suitable telemetry system is available from Noraxon U.S.A., Inc. as the Telemyo system, comprising a battery-operated wearable transmitter. Another suitable telemetry system is available from MIE Medical Research Ltd., as the MT8 Telemetry System. Yet another suitable telemetry system is disclosed in U.S. Pat. 5,704,351.

Biofeedback device 10 further includes a signaling element 24 operatively connected to sensing element 12 (and specifically receiving unit 16) so that signaling element 24 is able to provide a signal upon an occurrence of a predetermined electrical activity for the sphincter muscle. For the purposes of the present invention, "operatively connected" refers to a means of communication such that sensing element 12 may notify signaling element 24 when electrode 14 detects a predetermined or specified electrical activity of the sphincter muscle. "Operatively connected" may, for example, include a means of communication such as an electrical connection via a conductive wire or member, or via a transmitted signal such as radio frequency, infrared or another transmitted frequency communication. Accordingly, signaling element 24 may either be integrated with receiving unit 16 of sensing element 12 or a separate unit. It will therefore be appreciated that signaling element 24 may be associated with an article of the person's clothing, a separate element wearable by the person, associated with a piece of furniture, or a separate table-based device.

Figure 2:
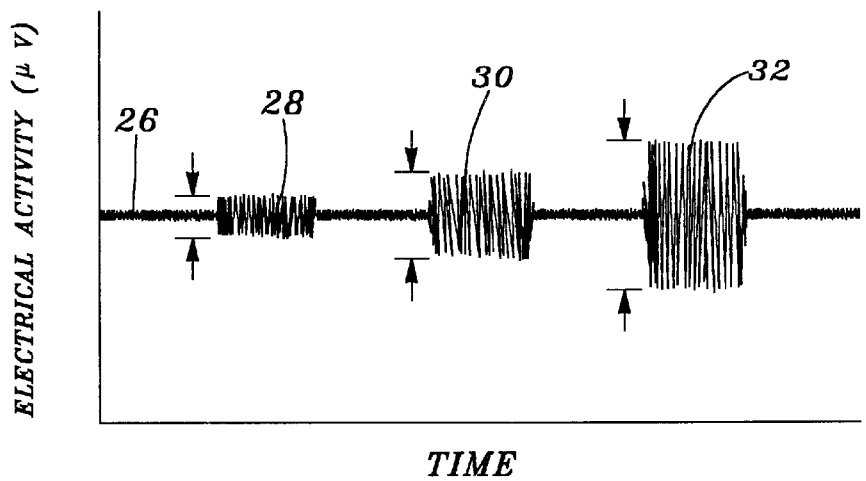
FIG. 2 is a graph depicting a first example of electrical activity of a sphincter muscle sensed by the sensing element of the biofeedback device of FIG. 1.
Figure 3:
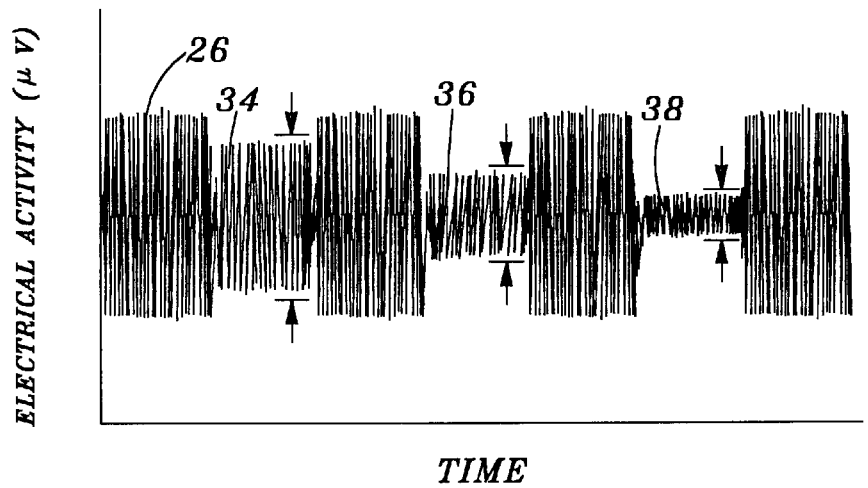
FIG. 3 is a graph depicting a second example of electrical activity of a sphincter muscle sensed by the sensing element of the biofeedback device of FIG. 1.

By "predetermined electrical activity" or "specified electrical activity," it is meant any electrical activity of the sphincter muscle which indicates the impending elimination of bodily waste. It will be appreciated that the predetermined electrical activity may be a designated change in electrical values or a designated absolute electrical value. As seen in FIGS. 2 and 3, where graphs depict the electrical activity of the sphincter muscle being sensed in terms of voltage versus time, certain changes in a basal electrical activity for such sphincter muscle are identified. It will be seen that the basal electrical activity for the sphincter muscle is denoted by a signal 26, where signal 26 is established by sensing the sphincter muscle over a specified time period (e.g., several hours to several days). Since relatively minor changes in the basal electrical activity 26 for the sphincter muscle can be due to any of several causes (i.e., movement of the person, anxiety, etc.), it is important to distinguish an impending voiding event therefrom. This is accomplished by setting a designated threshold amount in which the basal electrical activity is modified.

One preferred manner of determining the predetermined electrical activity is to detect the contraction of the sphincter muscle. It is well known, for example, that contraction of the external anal sphincter is a signal of imminent or potential defecation. In continent adults and older children and babies, the rapid filling of the rectum with feces from the sigmoid junction (i.e., the lower region of the colon) causes the external anal sphincter to reflexively (i.e., involuntarily) contract. This reflex is referred to as the anorectal reflex. A sharp increase in the external anal sphincter muscle activity accompanies the contraction of the external anal sphincter and is detectable as an electrical signal via electrode 14 of the present invention. As indicated in FIG. 2, the increase in external anal sphincter electrical activity that signals rectal filling (i.e., the designated threshold amount of increase from the basal electrical activity thereof) is preferably at least about two times the basal external anal sphincter activity (identified by reference numeral 28), but may be at least about three times the basal electrical activity (identified by reference numeral 30). Optimally, the increase in external anal sphincter electrical activity is at least about five times the basal electrical activity or more (identified by reference numeral 32).

In another preferred embodiment, electrode 14 detects sharp decreases in, or the absence of, electrical activity of the sphincter muscle. Such decreases occur in the external anal sphincter muscle, for example, when it relaxes to open the rectal neck just prior to, or during, defecation. Generally, the electrical activity of the external anal sphincter muscle will drop sharply for at least several seconds as the muscles relax. The activity is at or close to zero immediately preceding and during the elimination process. In these embodiments (see FIG. 3), a predetermined electrical activity may be identified as precipitous drops in the basal electrical activity for the sphincter muscle, preferably decreases of greater than or equal to about 50% (identified by reference numeral 34). More preferably, the predetermined electrical activity may be identified as decreases of greater than or equal to about 75% of the basal electrical activity (identified by reference numeral 36), or optimally equal to about 95% of the basal electrical activity (identified by reference numeral 38).

Figure 4:
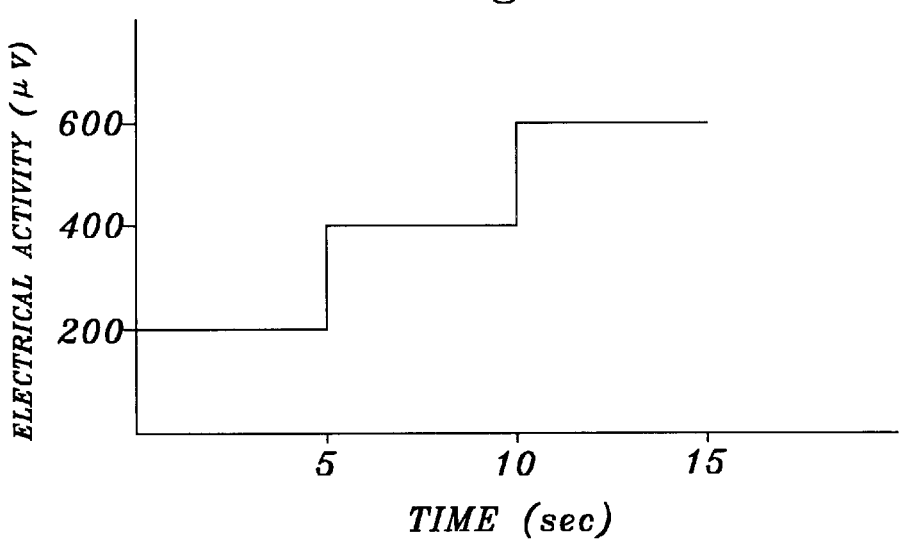
FIG. 4 is a graph depicting a third example of electrical activity of a sphincter muscle sensed by the sensing element of the biofeedback device of FIG. 1.

In a third embodiment, the predetermined electrical activity of the sphincter muscle is deemed equivalent to a signal having a designated electrical value for at least a designated time period (see FIG. 4). These parameters may be either preset within receiving unit 16 (i.e., based on a typical or average electrical value and duration of a contraction) or programmed therein so as to reflect an appropriate electrical value and duration for a particular incontinent person. Accordingly, the designated electrical value will preferably be at least about 200 microvolts and, more preferably, at least about 400 microvolts. Optimally, the designated electrical value for a signal reflective of a predetermined electrical activity for a sphincter muscle is at least about 600 microvolts. With respect to the designated time period or duration for the signal at the designated electrical value to be considered the predetermined electrical activity, it is preferred that the designated electrical value be maintained for at least about one second and more preferably for at least about three seconds. Optimally, the time duration at the designated electrical value will be for at least about five seconds.

With respect to the signal provided by signaling element 24 when the predetermined electrical activity for the sphincter muscle occurs, it will be appreciated that such indication may be made by a visual indicator 40 (e.g., an LED or other light signal), an aural indicator 42 (e.g., an alarm or other noise making device), or a tactile indicator 44 (e.g., a vibrating mechanism). In addition, in certain embodiments it is preferred that the signal, regardless of the form utilized, provided by signaling element 24 increase and decrease in intensity as the sphincter muscle increases and decreases in electrical activity once the applicable threshold change in the basal electrical activity or designated electrical value is reached. In this way, the indication becomes brighter visually, louder aurally, or greater tactilely.

While biofeedback device 10 as presently described is able to predict when an impending elimination of bodily waste is about to occur and provide an alert or warning before such event, it is also contemplated that device 10 be able to assist an incontinent person in achieving a contraction of his/her sphincter muscle. Accordingly, signaling element 24 of biofeedback device 10 preferably is able to provide a signal that indicates to the incontinent person and/or a caregiver that an intentional, voluntary contraction of the sphincter muscle should be attempted and/or continued. In this way, direct feedback is given which signifies the state of the incontinent person's sphincter muscle and whether he/she will have time to get to a toilet or other facility.

Alternatively, the signal provided may be a stimulus to a portion of the incontinent person's anatomy so as to achieve a temporary contraction in the sphincter muscle. More specifically, a stimulus device 46 connected to receiving unit 16 and electrode 14 is able to deliver an electrical impulse (or electrical stimulation) as required to the perianal skin to induce the temporary contraction and have it function as a continence aid. (This process may be alternatively referred to as dynamic gracilopasty nerve stimulation in the medical literature.) For the purpose of this invention, the electrical activity herein referred to as the electrical activity of the sphincter muscle may additionally include electrical activity from other pelvic floor muscles associated with the external anal sphincter muscle. This approach may also be applied to the external urethral sphincter muscle.

The electrical impulse may consist of one or more pulses of electricity or may be a continuous impulse. While the maximum strength of the electrical impulse may be as high as about 35 volts, the electrical impulse preferably has a voltage in the range of about 0.05 to about 5 Volts and more preferably in the range of about 0.3 to about 1 Volt. Preferably, the electrical impulse current is in the range of about 0.1 to about 100 milliamperes. Preferably, the stimulation frequency is in the range of about 10 to about 100 Hertz, more preferably in the range of about 20 to about 80 Hertz, and even more preferably in the range of about 60 to about 80 Hertz. If the impulse is a pulse (one or a multiplicity of pulses), the duration of each pulse is preferably in the range of about 0.1 to about 5 milliseconds and more preferably in the range of about 0.5 to about 1 millisecond. In certain embodiments where the impulse comprises a multiplicity of pulses, the entire set of pulses, or "pulse train," may have a duration of about 0.1 second to about 15 seconds with an interval between pulse trains of between about 1 second and about 60 seconds. Preferably, the electrical stimulation voltage, frequency, the number and frequency of pulses in a pulse train, and the number and duration of and spacing between pulse trains may be modified and/or controlled by the incontinent person or the caregiver therefor. Any electrical circuit as known in the art capable of meeting these parameters may be used to deliver or control the electrical stimulation to the external anal sphincter or other body location. For example, a 3 volt watch battery with a pulse generating system may operatively be connected with electrode 14 of sensing element 12, which can then be used to deliver one or more electrical impulses to the incontinent person's skin in the perianal region. One exemplary electrical stimulation device is the Prosper e.i.s. 5000 system available from the Dr. Rowedder Biomedizinische Geraete in Muehbrook, Germany. This device may be alternatively used with an adhesive surface electrode as described herein.

In alternative embodiments of stimulation (i.e., contraction) of the external sphincter muscles as a continence aid, the signal from sensing element 12 may be directed to another site on the incontinent person's body to elicit the anorectal reflex. For example, sensing element 12 may trigger an electrical or mechanical stimulation of the perineal skin, the skin at the back of the incontinent person's knee, the sole of the foot, or any other site that results in the expression of the anorectal reflex.

It will be appreciated that the components of biofeedback device 10 undergo certain process steps when used to predict an impending elimination of bodily waste in an incontinent person or to train an incontinent person to control the reflex action of his/her sphincter muscle. In order to better understand such processes, the flow chart of FIG. 5 is provided and explained hereinafter.

Figure 5:
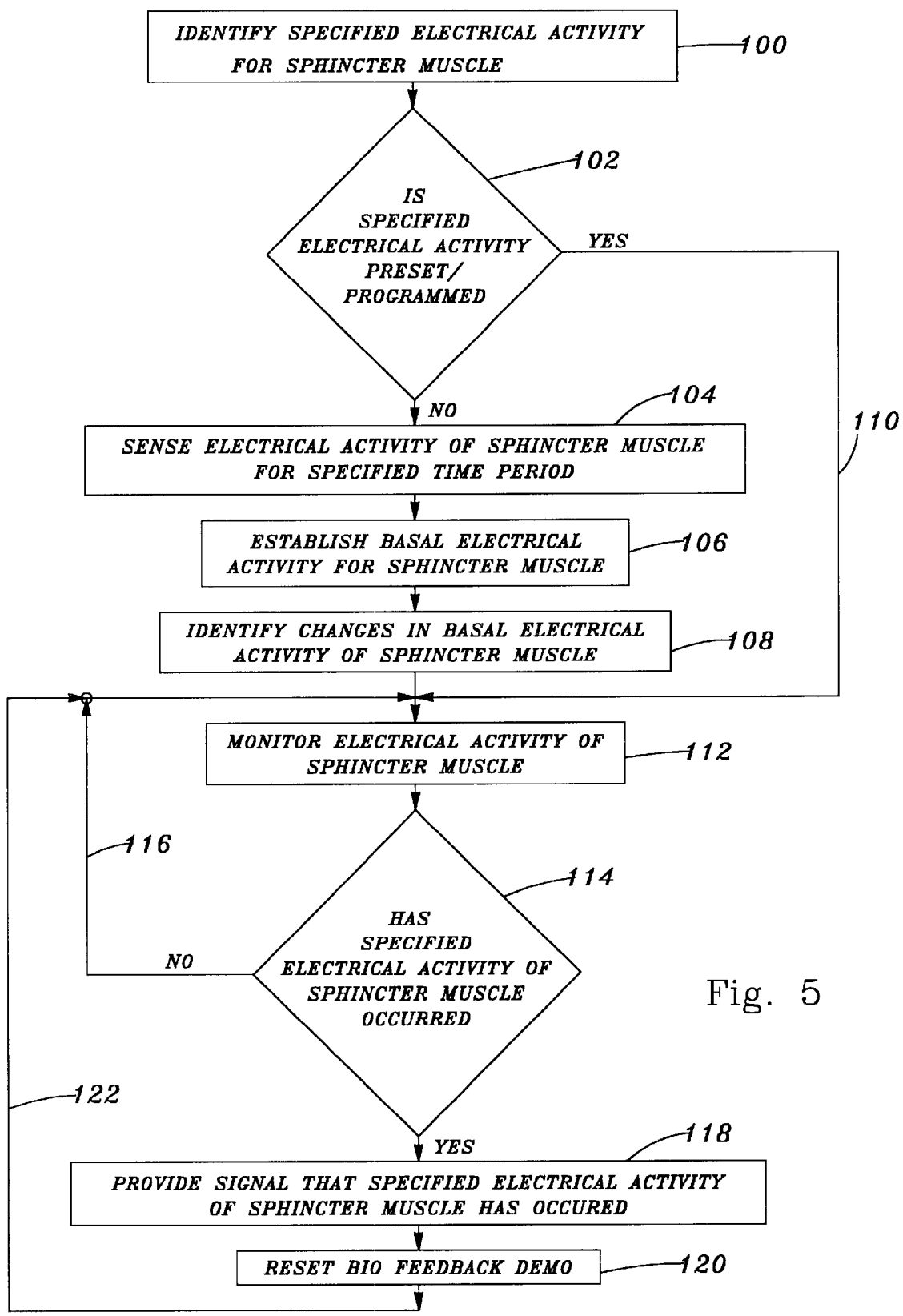
FIG. 5 is a flow chart depicting the process steps performed by the biofeedback device depicted in FIG. 1 when used for predicting an impending elimination of bodily waste in an incontinent person or assisting an incontinent person in achieving a contraction of his/her sphincter muscle.

With respect to the process of predicting an impending elimination of bodily waste in an incontinent person, FIG. 5 indicates that biofeedback device 10 first identifies a specified electrical activity for a sphincter muscle of the incontinent person correlating to a contraction thereof (box 100). Since the specified electrical activity may be either a designated change in the electrical level or a designated electrical value for the sphincter muscle, it wig be seen that receiving unit 16 of sensing element 12 determines if the specified electrical activity is a preset/programmed electrical value (decision box 102). If the answer is negative (i.e., the specified electrical activity is a designated change in electrical level), then sensing element 12 senses the electrical activity for a sphincter muscle of the incontinent person by means of electrode 14 and receiving unit 16 for a specified time period (box 104). In this manner, sensing element 12 is able to establish a basal electrical activity 26 for the sphincter muscle (box 106) which is indicative of the typical electrical activity experienced by such sphincter muscle during normal (steady state) operation. Next, changes in the basal electrical activity for the sphincter muscle are identified which correlate to an impending elimination of bodily waste (box 108). Since a sharp increase in sphincter muscle activity accompanies the contraction thereof during the anorectal reflex (e.g., anywhere from at least about two times to at least about five times the basal electrical activity) or a sharp decrease in sphincter muscle activity occurs when the sphincter muscle relaxes to open the rectal neck just prior to or during defecation (e.g., anywhere from about a 50% to about a 95% decrease of the basal electrical activity), such increases or decreases in electrical activity are used to identify impending voiding events. If the answer to decision box 102 is positive, it will be noted that the process steps identified in boxes 104, 106, and 108 are skipped via line 110.

Once a specified electrical activity is associated with an impending voiding event, biofeedback device 10 monitors the electrical activity of the sphincter muscle (box 112) and determines whether such specified electrical activity occurs for the sphincter muscle (decision box 114). So long as no specified electrical activity of the sphincter muscle is detected (i.e., a negative response to decision box 114), biofeedback device 10 preferably continues to monitor (either continuously or at predetermined intervals) the electrical activity of the sphincter muscle (see feedback 116). Should a specified electrical activity for the sphincter muscle be detected (i.e., a positive response to decision box 114), it is preferred that biofeedback device 10 provide a signal (visual, aural, and/or tactile) thereof (box 118). Such signal, whether located adjacent or remote to the incontinent person, is useful for alerting the incontinent person and/or a caregiver as to an impending voiding event and enables some action to be taken prior thereto. After a specified warning time in which the indication is maintained, biofeedback device 10 preferably resets (box 120) and the electrical activity of the sphincter muscle is then monitored by sensing element 12 once again (feedback line 122).

With regard to the process for assisting an incontinent person in achieving contraction of his/her sphincter muscle by means of biofeedback device 10, it will be understood from the process step in box 100 of FIG. 5 that the specified electrical activity for the sphincter muscle correlates to an impending elimination of bodily waste. While this may be accomplished in other ways, it is preferred that this be done by establishing a designated electrical value by presetting or programming receiving unit 16 (inferred from decision box 102) or establishing a designated change in the electrical level in the manner described hereinabove for boxes 104, 106 and 108 (i.e., sense the electrical activity of the sphincter muscle for a specified time period, establish a basal electrical activity for the sphincter muscle during normal operation, and identify changes in the basal electrical activity for the sphincter muscle correlating to an impending elimination of bodily waste, respectively). Of course, the steps detailed in boxes 104, 106 and 108 are skipped via line 110 if the answer to decision box 102 is positive. Once the specified electrical activity of the sphincter muscle has been determined, biofeedback device 10 (through electrode 14 and receiving unit 16) monitors the electrical activity of the sphincter muscle (box 112). Next, biofeedback device 10 determines whether any specified electrical activity of the sphincter muscle occurs (decision box 114). If the answer is negative, biofeedback device 10 returns to the step of monitoring the electrical activity of the sphincter muscle (feedback line 116). Should a specified electrical activity of the sphincter muscle occur, however, a signal is provided to assist the incontinent person in achieving a contraction of the sphincter muscle (box 118). While the signal may take many forms, including electrical stimulation as detailed hereinabove, it is apparent that assisting a person to have an intentional, voluntary contraction functions as a continence aid. After the signal is provided in the manner programmed for biofeedback device 10, the device 10 is reset (box 120) and returned to the monitoring function (feedback line 122).

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention.

What is claimed is:

1. A biofeedback device for signaling an impending elimination of bodily waste, the biofeedback device comprising:

(a) a sensing element adapted to be in contact with a body so as to detect an electrical activity of a sphincter muscle surrounding a bodily opening; the sensing element comprising a receiving unit adapted to:
(i) establish a basal electrical activity for the sphincter muscle by monitoring the electrical activity over a specified time period;
(ii) identify a correlation between a change in the basal electrical activity and an elimination of bodily waste, the change constituting a specified electrical activity correlating to a voluntary contraction of the sphincter muscle;
(iii) determine whether the specified electrical activity recurs during continued monitoring; and
(b) a signaling element operatively connected to the receiving unit, the signaling element adapted to provide a signal upon the determination by the receiving unit that the specified electrical activity has recurred.

2. A biofeedback device for signaling an impending elimination of bodily waste, the biofeedback device comprising:
(a) a sensing element adapted to be in contact with a body so as to detect an electrical activity of a sphincter muscle surrounding a bodily opening; the sensing element comprising a receiving unit adapted to:
(i) establish a basal electrical activity for the sphincter muscle by monitoring the electrical activity over a specified time period;
(ii) identify a correlation between a change in the basal electrical activity and an elimination of bodily waste, the change constituting a specified electrical activity;
(iii) determine whether the specified electrical activity recurs during continued monitoring;
(b) a signaling element operatively connected to the receiving unit, the signaling element adapted to provide a signal upon the determination by the receiving unit that the specified electrical activity has recurred; and
(c) a device for providing a stimulus to a portion of the user's anatomy so as to achieve a temporary contraction in the sphincter muscle.

3. The biofeedback device of claim 2, wherein the stimulus is applied to at least one of the following areas to achieve a temporary contraction in a sphincter muscle associated therewith: perianal skin and urethral skin.

4. The biofeedback device of claim 2, wherein the stimulus is an electrical stimulation having a voltage in a range of about 0.1 Volts to about 5 Volts.

5. The biofeedback device of claim 2, wherein the stimulus is an electrical stimulation having a current in a range of about 0.1 milliampere to about 100 milliamperes.

6. The biofeedback device of claim 2, wherein the stimulus is an electrical stimulation having a frequency in a range of about 10 Hertz to about 100 Hertz.

7. The biofeedback device of claim 2, wherein the stimulus is an electrical stimulation having at least one pulse.

8. The biofeedback device of claim 7, said pulses of said electrical stimulation having a range in duration of about 0.1–1.0 millisecond.

9. The biofeedback device of claim 7, said pulses of said electrical stimulation comprising a pulse train having a duration of about 0.1 second to about 15 seconds.

10. A method of assisting an incontinent person in achieving a contraction of his/her sphincter muscle, comprising the following steps:
(a) identifying a specified electrical activity for said sphincter muscle correlating to an impending elimination of bodily waste;
(b) monitoring electrical activity of said sphincter muscle;
(c) determining whether said specified electrical activity for said sphincter muscle has occurred; and
(d) providing a signal upon occurrence of said specified electrical activity.

11. The method of claim 10, said signal being an indication to said incontinent person when contraction of said sphincter muscle is attempted voluntarily.

12. The method of claim 10, wherein said signal is at least one of the following: a visual signal, an aural signal, and a tactile signal.

13. The method of claim 12, wherein said signal provided increases and decreases in intensity as said sphincter muscle increases and decreases, respectively, in electrical activity.

14. The method of claim 10, wherein said signal is provided at a location remote from said incontinent person.

15. The method of claim 10, wherein said specified electrical activity is a signal having an electrical level in a range of at least about 200–600 microvolts for at least a predetermined time period.

16. The method of claim 10, wherein specified electrical activity is a signal having a designated electrical level for a predetermined time period in a range of at least about 1–5 seconds.

17. The method of claim 10, said signal being a stimulus to a portion of the incontinent person's anatomy so as to achieve a temporary contraction in said sphincter muscle.

18. The method of claim 17, wherein the stimulus is applied to at least one of the following areas to achieve a temporary contraction in a sphincter muscle associated therewith: perianal skin and urethral skin.

19. The method of claim 17, wherein the stimulus is an electrical stimulation having a voltage in a range of about 0.1 Volts to about 5 Volts.

20. The method of claim 17, wherein the stimulus is an electrical stimulation having a current in a range of about 0.1 milliampere to about 100 milliamperes.

21. The method of claim 17, wherein the stimulus is an electrical stimulation having a frequency in a range of about 10 Hertz to about 100 Hertz.

22. The method of claim 17, wherein the stimulus is an electrical stimulation having at least one pulse.

23. The method of claim 22, said pulses of said electrical stimulation having a range in duration of about 0.1–1.0 millisecond.

24. The method of claim 22, said pulses of said electrical stimulation comprising a pulse train having a duration of about 0.1 second to about 15 seconds.

25. The method of claim 10, said identifying step further comprising:
(a) sensing the electrical activity of said sphincter muscle for a specified time period;
(b) establishing a basal electrical activity for said sphincter muscle; and
(c) identifying changes in said basal electrical activity for said sphincter muscle correlating to an impending elimination of bodily waste.

26. The method of claim 17, wherein said stimulus can be deactivated.

27. The method of claim 25, wherein said specified electrical activity corresponds to an increase in said basal electrical activity for said sphincter muscle in a range of at least 2–5 times.

28. The method of claim 25, wherein said specified electrical activity corresponds to a decrease in said basal electrical activity for said sphincter muscle in a range of at least 50–95%.

* * * * *

UNITED STATES PATENT AND TRADEMARK OFFICE
CERTIFICATE OF CORRECTION

PATENT NO.      : 6,498,953 B2
DATED           : December 24, 2002
INVENTOR(S)     : Donald Carroll Roe et al.

It is certified that error appears in the above-identified patent and that said Letters Patent is hereby corrected as shown below:

Column 1,
Line 33, delete "Coiling" and insert therefor -- Colling --.

Column 7,
Line 35, delete "wig" and insert therefor -- will --.

Signed and Sealed this

Twenty-fourth Day of August, 2004

JON W. DUDAS
*Director of the United States Patent and Trademark Office*